US012802789B2

(12) United States Patent
Horton et al.

(10) Patent No.: US 12,802,789 B2
(45) Date of Patent: Nov. 17, 2026

(54) AUTOMATIC MEDICAL DEVICE PATIENT REGISTRATION

(71) Applicant: BIOTRONIK SE & Co. KG, Berlin (DE)

(72) Inventors: James Horton, Portland, OR (US); Dean Bergstrom, West Linn, OR (US); Rainer Joerg Grosskopf, Portland, OR (US); Dirk Kleeblatt, Berlin (DE); Thorsten Wenzlaff, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 591 days.

(21) Appl. No.: 17/884,953

(22) Filed: Aug. 10, 2022

(65) Prior Publication Data

US 2023/0047795 A1 Feb. 16, 2023

Related U.S. Application Data

(60) Provisional application No. 63/232,858, filed on Aug. 13, 2021.

(30) Foreign Application Priority Data

Oct. 18, 2021 (EP) .................................... 21203161

(51) Int. Cl.
*G16H 10/60* (2018.01)
*G16H 40/40* (2018.01)
*G16H 40/67* (2018.01)

(52) U.S. Cl.
CPC ............. *G16H 10/60* (2018.01); *G16H 40/40* (2018.01); *G16H 40/67* (2018.01)

(58) Field of Classification Search
CPC ......... G16H 10/60; G16H 40/40; G16H 40/67
See application file for complete search history.

(56) References Cited

U.S. PATENT DOCUMENTS

| | | | | |
|---|---|---|---|---|
| 6,598,083 | B1 * | 7/2003 | Remer | H04L 63/0272 726/28 |
| 7,616,559 | B2 * | 11/2009 | Thompson | H04L 63/166 370/223 |
| 9,773,060 | B2 * | 9/2017 | Gerst | G16H 40/67 |
| 11,443,838 | B1 * | 9/2022 | Cordonnier | G16H 50/20 |
| 2010/0222845 | A1 * | 9/2010 | Goetz | G16H 10/60 607/59 |
| 2018/0060520 | A1 * | 3/2018 | Degen | G16H 40/67 |
| 2023/0245734 | A1 * | 8/2023 | Yoder | G16H 10/60 705/2 |

* cited by examiner

*Primary Examiner* — Quan Zhen Wang
*Assistant Examiner* — Mancil Littlejohn, Jr.
(74) *Attorney, Agent, or Firm* — FBT GIBBONS LLP

(57) ABSTRACT

A data system (100) is used for managing an information associated with an implantable device (IMP). The data system includes the implantable device. The data system is configured as a distributed database to store the information in two or more nodes of the data system. The implantable device is configured as one of the two or more nodes.

14 Claims, 6 Drawing Sheets

Device details

Device
Prospera

Decive Serial number
868095432

Clinician details

Following clinician name implanting clinician name

Clinician notes

This text field is to fit 500 characters in this space. For example: Patient goal is walking >1 mile and bending down to play with grandkids. Finds paresthesia <40 Hz very unpleasant. Generally low thresholds-- always use 0.1 mA steps. Is worried about jolts during programming. Get him sitting comfortably before paresthesia testing. Has been happy with system but is always worried about the pain coming back. Have had to educate on charger multiple times-- Include wife Jane in all training discussions.
7
8
9

Clinic details

Look up clinic

Clinic name
Very good clinic and hospital

Clinic Phone
1 123 4567890

Clinic address line1
Anyplace anywhere

Clinic city
Somecity

Clinic state / province / region
WY

Clinic zip / postal code
95229

Clinic country
USA

FIG. 2B

AUTOMATIC MEDICAL DEVICE PATIENT REGISTRATION

TECHNICAL FIELD

The present invention generally relates to a data system and an implantable device and a method, particularly for managing an information associated with the implantable device.

BACKGROUND

Various medical device systems have long been known. A common medical device system may comprise a medical device for facilitating therapies and/or monitoring a patient, as well as further system components for specific tasks associated with the operation of the medical device. Usually, the further system components may be used for managing information regarding the medical device (e.g. for adapting a medical device setting, registering a patient, storing medical device information, storing medical/clinical data, analyzing medical/technical data, remote patient monitoring, etc.). Notably, the further system components may be implemented by hardware (e.g. a user interface device, a server, a database storage unit, etc.) and/or software (e.g. an analysis program, a database management software, etc.).

In particular, medical device systems are known in the realm of implantable devices (e.g. implants such as a pacemaker, a cardioverter-defibrillator, a neurostimulator, an implantable sensor device, etc.) since their operation may require sophisticated medical, as well as technical supervision over a prolonged period of time to ensure the wellbeing of a patient having the implant.

Notably, current medical device systems may comprise relatively isolated system components with limited and/or no interconnectivity between them. For example, a common medical device system may resemble a setup of various segregated subsystems wherein only the components of one subsystem may be connected for information exchange (e.g. automated data sharing, etc.). Hence, common medical device systems may require a manual intervention (i.e. a manual data/information input) simply for aligning the information among the unconnected subsystems or components of the medical device system. This may be necessary every time an information changes and/or a new information arises in the medical device system (e.g. a change of an implant component, a change of a supervising clinician, a new patient registration, a new implant registration, etc.). Hence, current approaches may require an inefficient use of manual labor which may lead to a number of deficiencies in the medical device system (e.g. data entry error, multiple redundant data entries, limited functionality of the medical device system due to unavailable information, etc.).

Hence, the currently known approaches do not lead to an optimum management of information of an implantable device in a medical device system.

SUMMARY

The aspects described herein address the above need at least in part.

A first aspect relates to a data system for managing an information associated with an implantable device. The data system may comprise the implantable device wherein the data system may be configured as a distributed database to store the information in two or more nodes of the data system. The implantable device may be configured as one of the two or more nodes. The data system may be used as a medical device system for managing information associated with the implantable device.

The above aspect may enable a system architecture wherein the implantable device may be coupled to one or more nodes (i.e. system components) of the data system for a convenient (automatic) information exchange according to the principles of a distributed database. For example, the distributed database may represent multiple interconnected nodes (i.e. system components) at different physical locations wherein the nodes may be connected by a network for communication among the nodes.

Common approaches of medical device systems may suffer from a severe lack of interconnectivity of its system components. In a common medical device system (e.g. a Cardiac Rhythm Management (CRM) system) there may be a number of different databases of (medical) data/information wherein the databases may be stored in different (physical) locations in the system (e.g. in different system components, system devices, etc.). For example, there may be a first database in the implantable device, a second database in a clinician programmer (CP), a third database implemented by a device manufacturer's medical device registry (MDRF), and/or (occasionally) a customer database maintained for the field support/sales force. For the most part, these databases may store different data/information and may not be necessarily communicatively coupled. For example, the clinician programmer may only connect with the implantable device when a face-to-face session occurs (e.g. at a clinical check-up meeting, etc.). In that example, only at this manual procedure a communicative coupling is available between these two system components which may enable a read out of implant data and/or adjusting implant settings by the clinician programmer. In a further example, a data entry made to the MDRF for recording key data of the implantable device may not be directly shared with any other system component in the system. To illustrate another example, the information in the customer database may exist in isolation and may only be adapted by a manual entry (e.g. from a field technician, a sales force, etc.).

The lack of interconnectivity may be even more pronounced when the outlined common medical device system comprises a remote service system for a remote monitoring of the patient and/or the implant, as may be common in the medical sector. Usually, the remote service system may comprise a central server which may be in communication with the implantable device via an external patient transceiver. In that example, the implantable device, the external patient transceiver and/or the central server of the remote service system may be communicatively coupled to share data/information between themselves. However, this common remote service system may be configured as a centralized database (e.g. with the central server operating as the central database). In that example, the system components of the common remote service system may still comprise different databases for their specific application requirements (e.g. the implantable device may have a different type of database than the central server). Notably, the outlined nodes of the common remote system may not be connected/coupled with the other system components of the common medical device system (e.g. the clinician programmer (CP), the MDRF and/or the customer database). Hence, in common approaches there may be no communication link available between all maintained databases in the medical device system.

This lack of interconnectivity in known approaches may lead to a variety of deficiencies in the medical device system since its system components may require information (e.g. from any database) in the medical device system which they cannot (automatically) access. For example, this may lead to a data entry redundancy since the same information has to be manually entered at multiple system components so that all (or most) system components have access to the same information. This may require an inefficient use of manual labor, as well as an increased time effort (e.g. the access to system components may be at multiple distanced locations with potentially different dedicated personnel for adjusting the information, etc.). Further, this may lead to an information entry error (e.g. the repetition of the same information entry process at multiple locations may eventually lead to erroneous data due to a human error). Further, this may lead to a data entry latency (e.g. information is not always available when it is needed as the various data entry steps may not occur concurrently). Another deficiency in common approaches may be a reduced compliance. For example, steps in the functioning of the medical device system may not occur if the required data is not available. For example, a large percentage of remote monitoring non-compliance may occur because the patient has not been registered and/or is incorrectly registered into the medical device system. This may lead to reduced satisfaction on the part of the patient and clinicians (e.g. a remote monitoring system has been provided, but is not able to function), increased labor spent by the clinician and the device manufacturer in debugging the remote support process, and/or in increased capital expenditures (e.g. expensive hardware is provided to the patient, but it cannot operate as it is not correctly configured) .

The inventive data system may at least in part reduce these known deficiencies. The underlying idea of the invention may be based on the concept that the implantable device operates as an (active) node of the distributed database due to the data system's configuration. For example, the distributed database may be considered as a collection of multiple databases storing data wherein the multiple databases may be physically spread across various nodes (i.e. system components). Each of the multiple databases may comprise the same data, partly the same data and/or different data. However, due to the interconnectivity and the communication among the nodes, in some examples, the data of the multiple databases may be accessed as one logical database from any node of the data system (or from a certain part of nodes of the data system). In another example, only certain data may be accessed from the logical database which may depend on the node requesting the data.

The inventors have thus constructed the data system such that the implantable device may function as a physical data storage location (i.e. one of the multiple databases) of the distributed database with communicative connections to at least one further node of the data system. The data system's configuration as a distributed database may ensure that the information associated with the implantable device may be (automatically) distributed via the communicatively coupled nodes of the data system. For example, the data system may be configured such that each node may store the information associated with the implantable device. According to the principles of a distributed database, the information may thus be replicated throughout the nodes of the distributed database to align the information at all nodes. This distributive character may ensure that a change of information at one node will be distributed through the further nodes of the data system. For example, the information associated with the implantable device may change or may be newly created at one of the two or more nodes of the data system. The data system may be configured that at least one further node is automatically updated with the changed (or newly created) information. This information update may be implemented by a replication process of the changed (or newly created) information. For example, the replication may be triggered by a node where the information was changed (or a node where the information was newly created). In an example, when the (existing) information is changed (i.e. updated) during the application a revision (e.g. a revision number) may be assigned to the changed information with respect to the prior existing information. For example, the revision number may be a counter wherein the newly created information may be assigned a revision number one and with each subsequent change (i.e. update) of this information the revision number may be incrementally increased (e.g. to revision number two, three, four, etc.). The replication of the information through the nodes of the data system may also be triggered in regular occurring intervals wherein the most current (latest) revision of the information may be determined in the data system with a subsequent replication of the most current information through the nodes of the data system.

The implantable device may be regarded as a core node (i.e. core system component) from a medical perspective (e.g. since it may be used for facilitating medical therapies (e.g. via electrical stimulations) and/or monitoring a patient from within the body). The information associated with the implantable device stored on the implantable device (i.e. the core node) may thus be used for special technical purposes (e.g. the information in the core node may be given a certain priority status when the information status is unclear, etc.). The invention may comprise that all nodes of the distributed database may be interconnected to the core node (e.g. by a direct communication link and/or indirectly via a plurality of nodes). This approach may ensure that the nodes of the data base system may not be communicatively segregated and/or isolated from the core node.

Apart from the physical or logical database of the implantable device that is part of the distributed database as outlined herein, the implantable device may have further storage means in order to store, for example, local settings, etc., that need not necessarily be known to other nodes in the system (e.g. these may vary within boundaries as set by the data in the distributed database, for example).

The nodes of the data system may be configured to communicate wirelessly (e.g. over electromagnetic waves, radio frequency, Wi-Fi, Bluetooth, NFC, etc.) and/or over a wired connection. Notably, the nodes may be implemented by hardware and/or software. For example, a node may comprise a device, an apparatus, a system, a computer program, etc.

In an example, the data system may comprise three or more nodes, four or more nodes, or five or more nodes.

The inventive concept may enable a variety of advantages. For example, the data system may be conveniently expanded with additional nodes (i.e. system components) wherein the information associated with the implantable device may be readily available due to the outlined mechanics of the distributed database. In addition, the information may be accessed from various nodes of the data system without a loss of information.

In an example, the two or more nodes (of the data system) may further comprise at least one of the following nodes: a user device for entering the information into the data system; a backend system. To illustrate some examples, the user device may be a laptop, a portable device (which may be adapted for a clinical environment), a tablet, a smartphone, a desktop PC, etc.

The backend system may be configured for enabling various peripheral data operations (e.g. further data storage, data analysis, management of the nodes of the data system, cryptographic operations, data log management, authentication processes, monitoring data of the nodes of the data system). In an example, the backend system may comprise various components (e.g. supplementary nodes implemented by hardware and/or software) to enable the peripheral data operations (e.g. the components of the backend system may comprise a processing unit, a storage medium, a transceiver, a computer, a cloud-based application, etc.). Notably, the backend system may deliver a server-side functionality to the data system (e.g. it may comprise a server, a database server, etc.). Thus, the backend system may be communicated to via a client-server model (e.g. the backend system or specific component thereof may be addressed via a uniform resource locator, an internet protocol address, etc.).

In an example, the data system and/or the user device may be configured such that the only entry point for entering new information and/or for changing information to the data system is the user device. This may ensure that the user device is the only node where any change of the information associated with the implantable device may be initiated. This may reduce data entry points (e.g. for entering the information) to the data system to a minimum. For example, the other nodes in the data system may be responsible for refreshing the information stored in their nodes when new information or newer revisions of existing information gets replicated to them.

In an example, the user device may comprise: a user interface for receiving the information; a storage unit for storing the information. The user device may further comprise a transmitter for transmitting the information to the implantable device over an initial communication link between the user device and the implantable device for storing the information in the implantable device. For example, the user interface may be configured such that a user may manually enter the information associated with the implantable device (e.g. the user interface may comprise a touchscreen, a keyboard, a mouse, a display, a computer interface, a webpage, etc.). The storage unit for storing the information may comprise any storage medium capable of storing data of the distributed database (e.g. the storage medium may comprise a semiconductor-, magnetic-, optical-based storage unit, e.g. a solid-state drive, a hard disk drive, etc.). The initial communication link between the user device and the implantable device may be implemented by a direct wireless communication path between said devices. In an example, the user device may be configured to establish the initial communication link with the implantable device (e.g. over an initial wireless pairing procedure based on Wi-Fi, Bluetooth, NFC, RF, MICS, etc.).

To illustrate an example, after the information was entered via the user interface (e.g. by a clinician) to the user device (and thus the data system) the information may be stored on the user device and immediately (and automatically) written to the implantable device over the initial communication link. This process may ensure that a newly created (or updated) information at the user device (node) will be immediately copied (e.g. replicated or duplicated) and written to the implantable device (node). Hence, this approach may enable an information redundancy since it may ensure that the newly created (or updated) information is available (instantly) at two nodes of the data system. In an example, the user device may be configured to block entering information into the data system if the initial communication link to the implantable device is not available. This may ensure that information can only be redundantly entered into the data system. For example, this may permit correction of information errors and/or increase the confidence of the information in the data system when different information associated with the implantable device is present at different nodes in the data system. The user device (node) and/or the implantable device (node) may thus be used for verifying the most current information in the data system. During application, the user device (node) and the implantable device (node) may not always be simultaneously coupled for communicating with the other nodes of the data system. However, due to the redundant design, access to either one of these nodes (i.e. the user device or the implantable device) may suffice to verify the most current information in the data system. In an example, the communication over the initial communication link may be encrypted. To that regard, the user device may encrypt the newly created (or updated) information and transmit the encrypted information to the implantable device. Accordingly, the implantable device may be configured to decrypt the encrypted (newly created or updated) information and store the corresponding decrypted information in the implantable device (e.g. in a storage medium comprised in the implantable device).

In an example, any node in the data system other than the user device and the implantable device may be configured to refresh the information stored in their respective nodes automatically in regular occurring time intervals (e.g. every week, every month, etc.) and/or upon triggers (e.g. by a request, an event, etc.). This may comprise determining the most current (i.e. latest) revision of the information by determining the revision number of the information stored in the user device and/or the implantable device. Subsequently, the nodes may refresh their information if their respective revision number is lower than the revision number stored in the user device and/or the implantable device.

In an example, the data system may be configured such that only the user device is allowed to transmit information to the implantable device for storing the information in the implantable device. Hence, the user device may be configured as the only node for creating/adapting the information in the implantable device. For example, the user device which is in-session with the implantable device over the initial communication link may be the only node that is allowed to transmit (e.g. write) the information to the implantable device. This approach may enable that the information redundancy in the user device and the implantable device (as outlined herein) may not be disturbed by another node which may try to transmit the information to the implantable device.

In an example, the data system may be configured such that the revision number of the information associated with the implantable device may always be the latest in the implantable device. In another example, the data system may be configured such that the information in the user device and the implantable device is defined as an effective version of the information. Hence, the information stored in the implantable device may (always) be considered the latest (or effective) information associated with the implantable device throughout the data system. The data system may thus implement a data update schema that ensures that the revision of the information that is stored in the implantable device will always be higher or equal to the revision of the corresponding information stored in another node. For example, the information in the implantable device may have the revision number three. Thus, according to the data update schema, any other node in the data system may not create (or comprise) an information with a revision number higher than three. For example, this may be considered when a replication process (or an update of the information) is initiated at a node wherein the node (or the data system) may check if the revision number of the replicated information (or the updated information) is higher than the revision number of the information stored in the implantable device. If the latter result is true, the node (or the data system) may not initiate the replication process (or the update of the information).

In an example, the user device may be a node to create an information with a higher revision number than currently present in the implantable device only while the initial communication link is established (since the information with the higher revision number may be immediately sent to the implantable device via the initial communication link). In another example, the updated revision number (e.g. an increase in revision number) may be first assigned to the information in the implantable device after the entered information was transmitted from the user device to the implantable device. In that example, after the revision number was updated in the implantable device, the revision number may be updated/created for the corresponding information stored in the user device. In that regard, the user device may first adjust the information (and its revision number) in the implantable device and (only) then accordingly adjust the information in the user device.

In an example, the user device may be configured to communicate the information to the backend system over a first communication path for storing the information in the backend system. For example, the first communication path may comprise a path originating from the user device wherein the information may be communicated from the user device to the backend system over a direct path and/or via one or more nodes of the data system. In that example, the information may be communicated from the user device to the backend system (if the first communication path is available) after the information was transmitted from the user device to the implantable device over the initial communication link (or possibly only after the implantable device has confirmed update of the information). In an example, the first communication path may not comprise the implantable device. The communication of the information over the first communication path to the backend system may comprise a replication process to replicate the information stored in the user device onto a storage medium comprised in the backend system. In an example, the user device may be configured for encrypting the information stored therein. The replication process may thus comprise transmitting an encrypted copy of the information to the backend system wherein the backend system may be configured to decrypt the received copy of the information to store it in the storage medium comprised in the backend system. The communication between user device and backend may comprise communication over the internet for example, including wireless communication of the user device, e.g. via WiFi, cellular technology (e.g. 3G, 4G, 5G, etc.), etc.

In an example, the implantable device may be configured to communicate the information to the backend system over a second communication path for storing the information in the backend system. For example, the second communication path may comprise a path originating from the implantable device wherein the information may be communicated from the implantable device to the backend system over a direct path and/or via one or more nodes of the data system. In that example, the information may be communicated from the implantable device to the backend system (if the second communication path is available) after the information was transmitted from the user device to the implantable device over the initial communication link. In an example, the second communication path may not comprise the user device. The communication of the information over the second communication path to the backend system may comprise a replication process to replicate the information stored in the implantable device onto a storage medium comprised in the backend system. In an example, the implantable device may be configured for encrypting the information stored therein. The replication process may thus comprise transmitting an encrypted copy of the information to the backend system wherein the backend system may be configured to decrypt the received copy of the information to store it in the storage medium comprised in the backend system.

In an example, the data system may be configured to instruct the implantable device to communicate the information over the second communication path, if the first communication path is not available. The inventive concept may thus ensure redundant communication of the information to the backend system. This approach may be enabled by the outlined information redundancy of the data system that ensures that the newly created (or updated) information is available (instantly) at the user device and the implantable device. To illustrate an example, the newly created (or updated) information may have been written to the user device and the implantable device over the initial communication link as outlined herein, wherein the user device may not subsequently have a communicative connection to the backend system (e.g. no direct or indirect communication link). The newly created (or updated) information may thus be sent from the implantable device over the second communication path which may minimize a time delay of synchronizing the information in the backend system. The newly created (or updated) information may thus not be backlogged at the user device or the implantable device if the first communication path is not available. This approach may ensure that a change of information in the data system (e.g. at the user device and/or implantable device) may "ripple" through the nodes over the two redundant communication paths (i.e. the first and second communication path) which may minimize the latency of information synchronization in the data system.

In an example, the second communication path may comprise communication from the implantable device to the backend system via a patient device. For example, the patient device may be communicatively coupled to the implantable device and/or may be configured as a node of the data system. The patient device may be configured for adjusting implant settings of the implantable device and may be operated by the patient having the implant. In an example, the patient device may be a portable patient remote device wherein the implantable device may be a neurostimulation device (e.g. a spinal cord stimulator, etc.). In that example, the patient device may be used to adjust therapy settings of the neurostimulation device (e.g. the intensity of the applied stimulation shocks, the therapy stimulation mode, etc.). The patient device may comprise a transceiver for enabling various (wireless) communication processes (e.g. for functioning as a node in the data system, for reading/writing data to the implantable device, etc.). For example, the wireless communication to the implantable device may be Bluetooth-based (or based on MICS, or any other communication using an electro-magnetic wave) wherein the communication to the backend system may be Wi-Fi based (or based on any other communication using an electro-magnetic wave, e.g. as outlined herein). In an example, the patient device may function as the intermediary node between the implantable device and the backend system for communication over the second communication path. To that regard, the implantable device may transmit the (encrypted) information to the patient device wherein the patient device may pack the (encrypted) information into a specific data format and transmit them to the backend system. Hence, the patient device may be configured as a relay node to relay the (encrypted) information received from the implantable device to the backend system. In another example, the patient device may use the same replication process as the user device for updating the information in the backend system.

In another example, the second communication path may comprise communication from the implantable device to a second user device, wherein the second user device may be communicatively coupled to the backend system. The second user device may be similar or identical in hardware (and/or software) design to the user device as outlined herein. To that regard, the implantable device may transmit the (encrypted) information to the second user device wherein the second user device may replicate said information to the backend system. This approach may be implemented when the first communication path is not available (e.g. when the user device is offline).

In an example, the data system may be configured to communicate the information over the second communication path after the initial communication link between the user device and the implantable device is terminated. For example, the initial communication link may be a wireless connection (e.g. a Bluetooth connection, a Wi-Fi connection, etc.) for transmitting the information from the user device to the implantable device. If that wireless connection is terminated (e.g. the Bluetooth connection is terminated, etc.) the implantable device may trigger transmitting the information (or replicating the information) via the second communication path to the backend system. In an example, the implantable device may trigger transmitting the information as soon as it has a connection to the patient device which may function as the relay node of the second communication path as outlined herein.

In another example, after the user device (for entering the information to the data system) has transmitted the information to the implantable device, the patient device and the implantable device may (automatically) connect (e.g. wirelessly, e.g. via Bluetooth, etc.) for transmitting the encrypted copy of the information to the backend system via the patient device over the second communication path. The implantable device may thus be configured to trigger the transmitting of the copy of the newly created (or updated) information to the backend system as soon as it has a connection with the patient device after the information was newly created (or updated) in the implantable device.

In an example, the information (associated with the implantable device) may comprise at least one information entity, wherein the at least one information entity may comprise at least one of the following: a patient identifiable information, a patient non-identifiable information, a follow-up information, an implantable device information, a lead system information. The patient identifiable information may comprise information that can (physically) identify a patient (e.g. a patient name, an address, a telephone number, etc.). The patient non-identifiable information may comprise information that may not directly identify a patient (e.g. a patient's database key, a reference to the corresponding patient identifiable information, a stimulation mode, etc.). The separation of the patient identifiable information and the patient non-identifiable information may enable that patient identifiers can be excluded for most actions (e.g. since the patient non-identifiable information may suffice). Both types of patient information may be classified as private data by the data system and may be stored separately to enable that database queries can exclude patient identifiers (e.g. so this data may not be stored in log files). In a further example, an (artificial) identifier may be used to map the patient identifiable information and the patient non-identifiable information. Further, the user device may create a follow-up information (object) for every face-to-face follow up (e.g. a doctor's appointment, etc.) and every remote follow up (i.e. a remote programming session) that a user may conduct for the patient. The follow-up information may comprise information about a patient's follow-up session (e.g. a start time, an end time, therapy settings that were programmed in a specific follow-up, a reference to the implantable device that was programmed, a reference to the clinician who performed the follow up, etc.). The implantable device information may comprise information on the implantable device (e.g. an implant model, an implant serial number, a hardware version of the implant, a software version of the implant). The lead system information may comprise information on the lead system of the implantable device (e.g. a lead type, a lead model, a lead serial number). The information may also comprise identifiers, references, relations to associated different information (entities) with each other.

A second aspect relates to an implantable device, wherein the implantable device is configured as a node of a distributed database to store an information associated with the implantable device that is also stored in at least one further node of the distributed database.

The implantable device may be part of a data system, wherein the data system may be configured as the distributed database to store an information associated with the implantable device in two or more nodes of the data system. The implantable device may be configured as one of the two or more nodes. Notably, the implantable device may thus be configured as a physical storage location of the information comprised in the distributed database and may be configured for communicating with at least one further node of the data system.

A third aspect relates to a method for managing an information associated with an implantable device. The method may comprise: entering the information into a user device; transmitting the information from the user device to the implantable device over an initial communication link; storing the information in the implantable device. The method may further comprise communicating the information from the user device to a backend system over a first communication path and/or communicating the information from the implantable device to the backend system over a second communication path.

The implantable device may be part of a data system which may be configured as a distributed database. The implantable device may be configured as a node in the distributed database. The backend system and/or the user device may be configured as further nodes of the distributed database.

In an example, the method may further comprise storing the information in the user device wherein the user device may be part of the data system (e.g. a node of the distributed database). In another example, the method may further comprise storing the communicated information in the backend system wherein the backend system may be part of the data system (e.g. a node of the distributed database).

In an example, the method may further comprise at least one of the following: communicating the information over the second communication path, if the first communication path is not available; communicating the information over the second communication path after the initial communication link between the user device and the implantable device is terminated. For example, the communicating of the information from the implantable device to the backend system may be implemented via one or more further nodes (e.g. a patient device) comprised in the database system.

In an example, the method may further comprise at least one of the following: relating information entities which are comprised in the information to each other and/or relating at least one information entity which is comprised in the information to at least one supplementary information entity which is comprised in the data system. For example, the following information entities (e.g., as outlined herein) may be related with each other: a patient identifiable information, a patient non-identifiable information, a follow-up information, an implantable device information, a lead system information. The at least one supplementary information entity may be comprised in the backend system and may be part of a supplementary database. For example, the supplementary information entity may comprise information on a name of a clinic, a name of a clinician, and/or additional patient data, etc.

In an example, the method may further comprise at least one of the following: communicating the information from the implantable device to the backend system over the second communication path via a patient device (which may be part of the data system); relating a patient device to the implantable device; relating a patient device to the information; relating a patient device to at least one information entity.

For example, the patient device may be configured to create an association information which may relate the patient device (e.g. via the patient device's serial number) to the implantable device (e.g. via the implantable device's serial number), e.g. pair patient device and implantable device. This relation may be established by the patient device when it initially connects with the implantable device.

The method may further comprise that the relating of the patient device to the information associated with the implantable device (or to the at least one information entity) is implemented by the backend system comprised in the data system. In an example, the patient device may be associated with a patient device information entity (e.g. which may comprise a patient's device serial number, a patient's devices identifier, etc.). Thus, the patient device may be related to another information by relating the patient device information entity to said information. In another example, the patient device (or patient device information entity) may be related to the information entities as outlined herein (e.g. the implantable device information, the patient identifiable information, the patient non-identifiable information, a follow-up information, a lead system information, etc.).

In an example, the method may further comprise communicating a request signal to the backend system by the patient device after it has paired (and thus associated itself) with the implantable device. In an example, the method may comprise specifying (patient unspecific) information entities (e.g. patient non-identifiable information, implantable device information, etc.) based at least in part on the request signal. The method may further comprise granting read access to the patient device to specific data/information comprised in the backend system (e.g. patient specific information entities, e.g. patient identifiable information, etc.).

It is noted that the method steps as described herein may include all aspects described herein, even if not expressly described as method steps but rather with reference to a system (or device or apparatus). Moreover, the devices as outlined herein may include means for implementing all aspects as outlined herein, even if these may rather be described in the context of method steps.

Whether described as method steps, computer program and/or means, the functions described herein may be implemented in hardware, software, firmware, and/or combinations thereof. If implemented in software/firmware, the functions may be stored on or transmitted as one or more instructions or code on a computer-readable medium. Computer-readable media include both computer storage media and communication media including any medium that facilitates transfer of a computer program from one place to another. A storage medium may be any available medium that can be accessed by a general purpose or special purpose computer. By way of example, and not limitation, such computer-readable storage media can comprise RAM, ROM, EEPROM, FPGA, CD/DVD or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor.

DESCRIPTION OF THE DRAWINGS

In the following, the Figures of the present disclosure are listed:

FIGS. 2*a-b* Schematic representation of an exemplary embodiment of a user interface of a user device in the data system for entering information associated with an implantable device.

DETAILED DESCRIPTION

Figure 1:
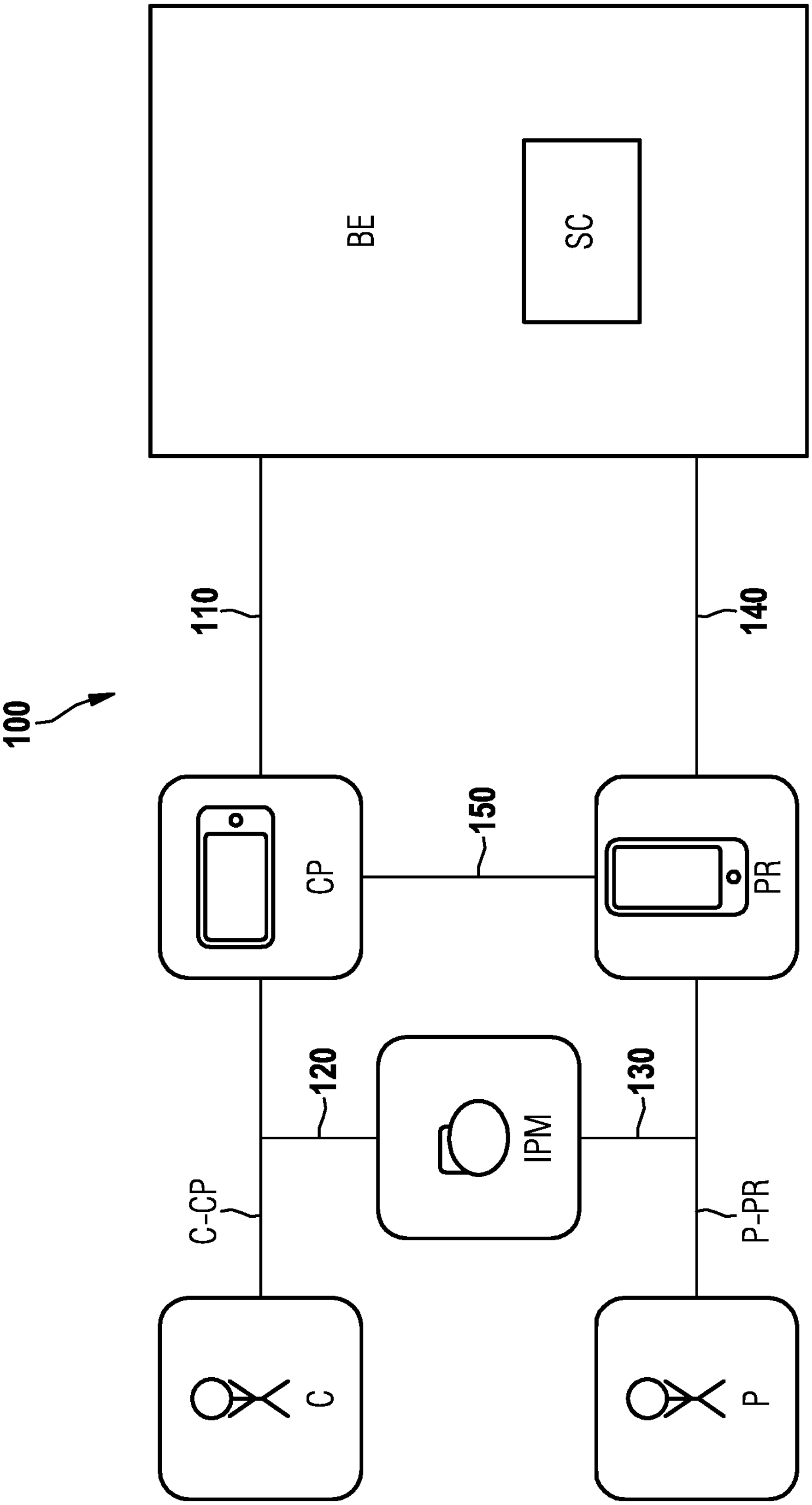
FIG. 1 Schematic representation of an exemplary embodiment of a data system according to the present invention.

FIG. 1 shows a schematic representation of an exemplary embodiment of a data system 100 according to the present invention. The data system 100 may comprise various nodes which may be communicatively interconnected. For example, the nodes of the data system 100 may comprise a user device CP, an implantable device IMP, a patient device PR, and/or a backend system BE. The user device CP may be a portable device (e.g. a tablet, a smartphone, etc.) and/or a stationary device (e.g. a desktop PC, a stationary medical device, etc.).

The implantable device IMP may comprise any implantable (medical) device (e.g. a pacemaker, a cardioverter-defibrillator, a cardiac monitor, a (neuro)stimulator, a spinal cord stimulator, an implantable sensor, a trial stimulator, etc.). Hence, the implantable device IMP may be implanted into a patient wherein the implantable device IMP may be configured as a node of the data system 100. The implantable device IMP may thus communicate with another node of the data system 100 that may reside outside of the patient's body (and/or another node residing inside of the patient).

The patient device PR may comprise a portable remote (comprising a user interface e.g. a keyboard, a display, a touchscreen, etc.) which may be operated by the patient. In an example, the patient device PR may comprise a transceiver for relaying the communication from the implantable device IMP to the other nodes of the data system 100.

The backend system BE may comprise various components (e.g. supplementary nodes implemented by hardware and/or software) and may be configured to enable various peripheral data operations, as outlined herein (e.g. further data storage, data analysis, management of the nodes of the data system 100, cryptographic operations, data log management, authentication processes, monitoring data of the nodes of the data system, remote monitoring of the implantable device IMP, etc.). Furthermore, the backend system BE may comprise various components to deliver a server-side functionality to the data system (e.g. a (database) server, a synchronization interface for coupling the information to the backend system's storage, etc.). In an example, the backend system may be accessed by addressing an according server uniform resource locator (URL). In an example, the backend system BE may comprise a service center SC which may function as a central data processing system to implement the main control/access unit of the backend system BE (e.g. the service center may trigger/control various components of the backend system to provide the needed functionality depending on a specific communication from the other nodes of the data system to the service center SC, etc.). When referring to the backend system BE it may also be understood as referring to the service center SC (comprised in the backend system BE) since the service center may control most operations that take place in the backend system BE. For example, the backend system BE may be configured to implement an authentication of the patient device (e.g. via the open-source solution Keycloak), an authentication of the clinician by an identity and access management (e.g. via the commercial solution Azure AD (which may be hosted by the company Microsoft)), a system for data replication between the nodes of the data system 100 (e.g. between the user device CP, the patient device PR and/or the service center SC) wherein the system for data replication may be implemented by open-source solution Couchbase (e.g. a Couchbase server comprised in the backend system BE), for example. The backend system may be further configured for alerting of mobile apps and/or mobile devices (e.g. which may be implemented by the commercial solution Firebase Cloud Messaging (which may be hosted by the company Google)).

In a further example, the data system 100 may comprise an application that may allow viewing, printing and/or exporting patient data and/or patient reports or other information stored in the distributed database (referred to as print application herein). In an example, the print application may be regarded as a virtual user device and may be referred to as a virtual node of the data system 100. The print application may be implemented by software (e.g. a computer program, an executable application, which may be accessed via a desktop computer, a mobile device, e.g., a (real) node of the data system 100). In an example, the print application may be accessible over the backend system BE, the user device CP and/or other data consumers of the backend system BE. The print application may allow viewing of the information (e.g. patient data) which is stored in a node of the data system 100 (e.g. the information in the user device CP, the backend system BE, the service center SC, etc.). In addition, it may allow printing and/or exporting the information (e.g. the patient reports). As an example, the data system 100 may thus comprise a printer (as a node) for printing the information. The exported information may be arranged in a specific report structure (e.g. for any easy readout) wherein various file formats may be conceivable of the exported information (e.g. a portable document format file, i.e. a PDF file, a txt file, a word processing format, etc.) wherein the exported information may be stored in the data system 100 and/or may be sent to another node of the data system 100 (or to an external device not comprised in the data system).

The nodes of the data system may be communicatively coupled by a wireless connection (e.g. via electro-magnetic waves, over Bluetooth, Wi-Fi, RF, etc.) and/or via a wired connection. For example, the communicative coupling between the nodes of the data system 100 may be implemented by public connectivity networks (e.g. public Wi-Fi, communication over the internet protocol) to enable an optimum communication access throughout the application.

In an example, each node may be directly communicatively coupled (e.g. via a direct connection) to every other node of the system via a direct communication path. In another example, as outlined in FIG. 1, the following node pairs may be configured for a direct communication: the user device CP and the backend system BE (via a communication path 110), the user device CP and the implantable device IMP (via a communication path 120 that may be referred to as an initial communication link), the implantable device IMP and the patient device PR (via a communication path 130), the patient device PR and the backend system BE (via a communication path 140), the user device CP and the patient device PR (via a communication path 150). The user device CP may be operated by a clinician C who may enter information into the user device CP and/or may read out information displayed on the user device CP (as indicated by the line C-CP in FIG. 1). The patient device PR may be operated by a patient P for adjusting implant settings (e.g. a neurostimulation parameter, a neurostimulation mode) (as indicated by the line P-PR in FIG. 1).

The data system 100 may be configured as a distributed database wherein each node of the data system 100 may comprise a database of the distributed database for storing information associated with the implantable device IMP. In an example, the data system 100 may be configured such that each node in the data system 100 may comprise (e.g. may store) the same information. The data system 100 (configured according to the principles of a distributed database) may thus ensure that a newly created information and/or an update of an existing information at any node may be replicated through the remaining nodes of the data system 100 (as outlined herein). This may be enabled by the interconnective character of the nodes in the data system 100 which is provided by the communicative coupling between the nodes.

In an example, the user device CP may be the only entry point for entering an information associated with the implantable device IMP to the data system 100. In an example, for entering the information over the user device CP, it may be mandatory (by the data system's 100 design) that the user device CP is communicatively coupled to the implantable device IMP over an initial communication link (e.g. the communication path 120, as outlined in FIG. 1).

The user device CP that is currently in-session with the implantable device IMP (e.g. over the communication path 120) may be the only node of the data system that is allowed to create and/or edit/update the information associated with the implantable device IMP stored in the distributed database. The user device CP may initially create information entities (e.g. patient entities) corresponding to the entered information associated with the implantable device IMP. The information may comprise the patient identifiable information, the patient non-identifiable information, and/or connected entities like a follow-up information, and implantable device information, a lead system information, etc., as outlined herein. In general, the information may comprise patient data for mapping the implantable device IMP to the patient having the implantable device IMP. In particular, the information may be entered to the data system (over the user device CP) when a new patient is registered to the implantable device. Subsequently, the user device CP may store the information (e.g. the information entities) in its own local database and transmit the information (e.g. over the communication path 120) to the implantable device IMP for storing it in the implantable device's IMP memory. The transmitting of the information to the implantable device IMP may be triggered immediately with the storing of the information in the user device CP.

This approach may ensure that data entry points to the data system 100 are limited to a minimum (e.g. only the user device CP) which may reduce system complexity, reduce erroneous and/or varying information throughout the data system, enable an optimized patient registration, reduce medical risks resulting from a false patient association to the implantable device IMP, etc. Moreover, this approach may ensure that the information can only be entered redundantly into two nodes of the data system (i.e. the implantable device CP and the patient device IMP). The newly created (or edited/updated) information entities may thus be (almost) instantly available at these two nodes (and thus database storage locations) wherein said two nodes may be referred to as the two origin nodes.

Subsequently, the information may be replicated through the nodes of the data system 100 over various paths to synchronize and/or align the information throughout the distributed database. For most application purposes, it may be necessary to replicate the information from the two origin nodes to the backend system BE (to enable the peripheral data applications as outlined herein). To that regard, the invention may enable two redundant paths for data replication of the entered information (at the two origin nodes).

In a first case, if the user device CP and the backend system BE (or in particular the service center SC) may have an available communication path (e.g. the direct communication path 110) when the information entities are created, the user device CP may replicate these information entities directly to a storage medium in the backend system BE (e.g. to a storage server, e.g. a Couchbase server) via this available communication path. For example, the communication path 110, which can be used in this case, may be referred to as a first communication path. In an example, the user device CP may use a replication process optimized for the storage medium in the backend system BE (e.g. a Couchbase Lite to Sync Gateway replication process if the storage medium is a Couchbase server) to push the documents to the backend system (or the service center SC). To that regard, the user device CP may have to be online (e.g. able to connect to the communicative coupling) and the backend system may have to be accessible (e.g. ready for data communication).

However, e.g., if the user device CP is offline when the information entities are created, the prior case of replication may not occur. In this situation (i.e. a second case), the information redundancy (due to the two origin nodes) in combination with the communication path redundancy to the backend system BE (which is available through the various interconnected nodes of the data system) may ensure an undisturbed replication of the data to the backend system BE, regardless. For example, the redundant communication to the backend system BE in the second case may comprise communication via the communication path 130, the patient device PR, and the communication path 140. To that regard, this (second case) redundant communication path may be referred to as the second communication path. Notably, in this case the implantable device IMP (as one of the two origin nodes) may transmit the information entities in an encrypted Home Monitoring (HM) message (e.g. in an implant encrypted message, such as an implant encrypted message document) to the patient device PR, which in turn may replicate the HM message to the backend system BE (e.g. to the Couchbase server). In the backend system BE, the encrypted HM message may be decrypted, parsed and/or processed. During parsing, the individual data blocks/parameters may be extracted from the message. During processing, the patient entities may be re-assembled from the message and written to the storage medium in the backend system BE.

In an example, the message parsing and message processing may be implemented in a model driven manner. For example, the backend system BE may comprise machine-readable models that define a model data structure (e.g. the raw/original structure of the information) and the corresponding (structure of the) information entity that is accordingly to be re-assembled. Hence, when a message comprising the information arrives in the backend system BE, the backend system BE may interpret said information into a (pre)defined structure of the information entity. This may be advantageous when a later generation (or a different type) of the implantable device IMP sends the information to the backend system BE in a different way (e.g. in a different raw/original structure). In that case, an additional machine-readable model may be simply added to the backend system BE wherein the additional machine-readable model may be configured for interpreting the different data structure into the existing structure of the according information entity. Hence, the information will be stored in the same structure in the backend system BE, regardless of the transmitted data structure. This approach may significantly reduce coding complexity and may minimize erroneous data.

In general, the HM Messages may be triggered at least once a day or based on additional triggers. In an example of the data system, the HM message may be triggered as soon as a connection between the user device CP and the implantable device IMP is terminated. This may ensure, that the redundant communication (via the second communication path) may be immediately initiated since a termination of the coupling (of the user device and the implantable device may indicate a new/updated information entry to the data system 100). In another example, a trigger for sending the HM message (comprising the information associated with the implantable device IMP) may be based on an actual storing of newly created (or updated) information in the implantable device IMP. Hence, if the user device CP has transmitted the information to the implantable device IMP (which in turn resulted in storing the information in the implantable device), the patient device PR and the implantable device IMP may connect (e.g. wirelessly via Bluetooth) wherein the IMP may produce an HM message which may be transmitted to the backend system BE via the second communication path. In a further example, a trigger for sending the HM message (comprising the information associated with the implantable device IMP) may be based on an event in which a connection to the patient device PR has been established (e.g. when the patient manually establishes a connection from the patient device PR to the implantable device IMP).

In another example, the patient device PR may replicate the information to the backend system BE by a replication process similar or identical to the replication process from the user device CP to the backend system BE as outlined for the first case (e.g. a Couchbase Lite to Sync Gateway replication process if the storage medium is a Couchbase server).

In an example, the entering of the information to the data system 100 may concurrently be accompanied by associating the patient device PR to the implantable device IMP (e.g. during a complete new patient registration, or a re-registration of the implant and the patient device PR in the data system 100). This may be necessary, if the patient device PR has not yet been associated with a (particular) implantable device IMP. Notably, the association process may not necessarily occur during a new patient registration but may also occur at other events (e.g. when the patient device PR initially connects to the implantable device IMP and/or every time the information is entered into the data system, etc.). Subsequently, the association process between the patient device PR and the implantable device is outlined.

To enable said association, the patient device PR may create a channel-access-request signal (e.g. which may be implemented by or comprise a database entity, a document, a computer instruction, etc.). The channel-access-request-signal may be subsequently replicated to the backend system BE for associating the patient device PR with the implantable device IMP. Further, the patient device PR may be associated with the (entered) information (e.g. information entities) through the association process which may be necessary to associate the patient device PR with the patient having the implantable device IMP.

In the first case (as outlined herein) the (entered) information (e.g. from a new patient registration) may have been already replicated to the backend system from the user device CP over the first communication path 110. Hence, the channel-access-request signal may arrive after the (entered) information (e.g. comprising patient information entities) has been stored in the backend system BE. Thus, the channel-access-request signal may be processed immediately such that the backend system BE may immediately create an association between the patient device PR sending the request (via the channel-access-request signal) and the patient.

In the second case (as outlined herein) or when the user device CP is offline, the (entered) information (e.g. from a new patient registration) may not have been transmitted yet to the backend system BE. Hence, the channel-access-request signal may be stored in the backend system BE until the information (e.g. comprising patient information entities) arrives. For example, the information may arrive when the user device CP can get online later to establish a connection to the backend system. Also, it is possible that the information may arrive later from the implantable device IMP over the second communication path (via the patient device), as discussed for the second case.

In an example, the channel-access-request signal may be triggered when the patient device PR first establishes a Bluetooth pairing with a new implantable device IMP. Subsequently, the according association process is outlined in more detail:

After provisioning, the patient device PR may not yet be associated with the (entered) information (e.g. a patient). Therefore, to associate itself with a patient, the patient device PR may need to get authorized for accessing patient data in the storage medium (e.g. a database of the distributed database) comprised in the backend system BE (e.g. access to a specific server channel of a data server may be necessary, e.g. a Couchbase channel). Initially, after provisioning, the patient device PR may create an association with the implantable device IMP through a short-distance wireless connection and create the according channel-access-request signal comprising said association information. Subsequently, the patient device PR may transmit (e.g. insert) the channel-access-request signal (e.g. implemented by a channel-access-request database entity) (in)to the storage medium comprised in the backend system BE. The channel-access-request signal may specify information entities that are not patient specific (e.g. patient non-identifiable information, implantable device information, and/or further patient device entities). Subsequently, the patient device PR may push the channel-access-request signal to a synchronization interface comprised in the backend system. For security purposes, information entity references in a channel-access-request signal may not be guessable (e.g. knowing a document identification of one patient, non-identifiable information entity may not allow an attacker to guess another document identification). The backend system BE (or its service center SC) may detect or process the channel-access-request signal which may trigger updating the authorizations for the account of the patient device PR. This may thus enable the authorized patient device PR to access/read patient specific data stored in the backend system. In an example, the authorization may comprise granting read access rights to certain database channels (e.g. Couchbase channels). The patient device PR may wait until the channel-access-request signal is processed. Subsequently, patient device PR may push patient-specific objects to the synchronization interface and/or may access patient-specific objects in the backend system via the synchronization interface.

To illustrate an example of the communication flow in the data system, a data flow of the (entered) information entities (e.g. patient entities) may start at the user device CP, wherein subsequently the information entities are communicated to the implantable device IMP. Consecutively, the information entities may be communicated to the backend system via the patient device PR. During the message parsing (e.g. of the HM message) the intermediate results (of the parsing process) may be written to the backend system (e.g. to a database server, e.g. a Couchbase server). The results of the further message processing may be subsequently stored in the backend system (e.g. in a database server, e.g. a Couchbase server).

Figure 2A:
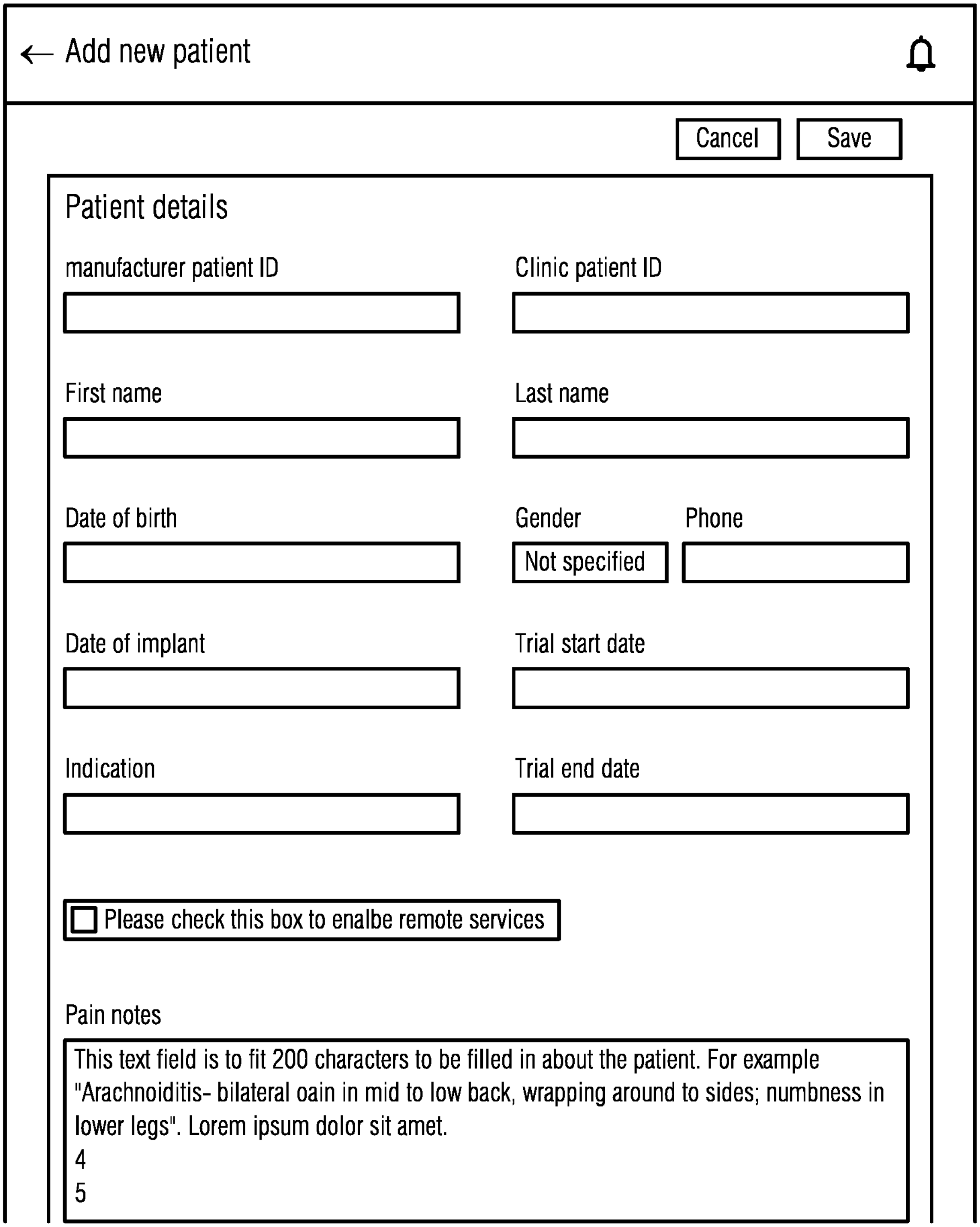

FIGS. 2*a*-*b* show a schematic representation of an exemplary embodiment of a user interface of the user device CP in the data system 100 for entering information associated with the implantable device IMP. As seen in FIG. 2 the user device CP may provide a patient registration general user interface (a patient registration GUI) that allows the user to enter (e.g. register) a new patient (or enter new information associated with the implantable device IMP) in the data system 100 and/or update existing information associated with the implantable device IMP in the data system 100. In the patient registration GUI, the user may enter the information (e.g. patient information) into various fields (e.g.

manufacturer patient ID, clinic patient ID, first name, last name, date of birth, information regarding health status, etc.) and may assign the patient to a group, a clinic and/or a clinician. Hence, during this creation process the patient may be initially assigned to the group (or the group may be updated). The assignment of the patient to a group, a clinic and/or a clinician may control access to the information by various users (e.g. a clinician may only have access to patients in specific groups they are assigned to or have access to by a (global) setting). The clinician access may be controlled by the administrative team in a separate process not described here (e.g. to set the (global) setting of the clinician access). When the patient registration GUI is filled out, the information (e.g. a patient entity, a patient identifiable information, a patient non-identifiable information) may be created as a database entity and related to other entities in the database (e.g. the patient entity may be related to the patient group that the patient is assigned to). Additional data created for that patient may be created as information entities in the database (e.g. a follow up information) by the user device CP, the patient device PR, and/or the backend system (e.g. by the service center SC) and related to that patient. This may give the user device CP, the patient device PR, the service center SC access to information about the patient. The patient entity and/or the associated entities may be replicated from the user device CP database to the backend system BE database, as outlined herein. Also, the patient registration GUI may display details of the IMP, such as its serial number.

As can be seen in FIG. 2*a* the patient registration GUI may comprise a check box for enabling remote services (e.g. as indicated by "Please check this box to enable remote services"). The check box may allow a user to activate or deactivate a remote monitoring service for the implantable device IMP (and thus the corresponding patient). The remote monitoring service may comprise various remote processes wherein the implantable device IMP and its data and/or settings are remotely accessed/adapted (e.g. during a remote follow-up session, a readout of relevant medical data, an adjustment of therapy settings, a technical check-up, etc.). For example, remote patient monitoring may be understood as a monitoring of a patient outside of conventional clinical settings (e.g. monitoring of a patient in his/her home, in a remote area, during his daily activities, etc.). The remote access to the implantable device IMP may be implemented by any remote (e.g. physically distant) node of the data system. In an example, the remote access may be requested by the backend system BE wherein the remote monitoring service may comprise various communication exchanges between the implantable device IMP and the backend system BE. The communication for the remote monitoring service may be implemented via the patient device PR (which may function as a relay transceiver to further nodes of the data system 100, and for example to the backend system BE).

Figure 3:
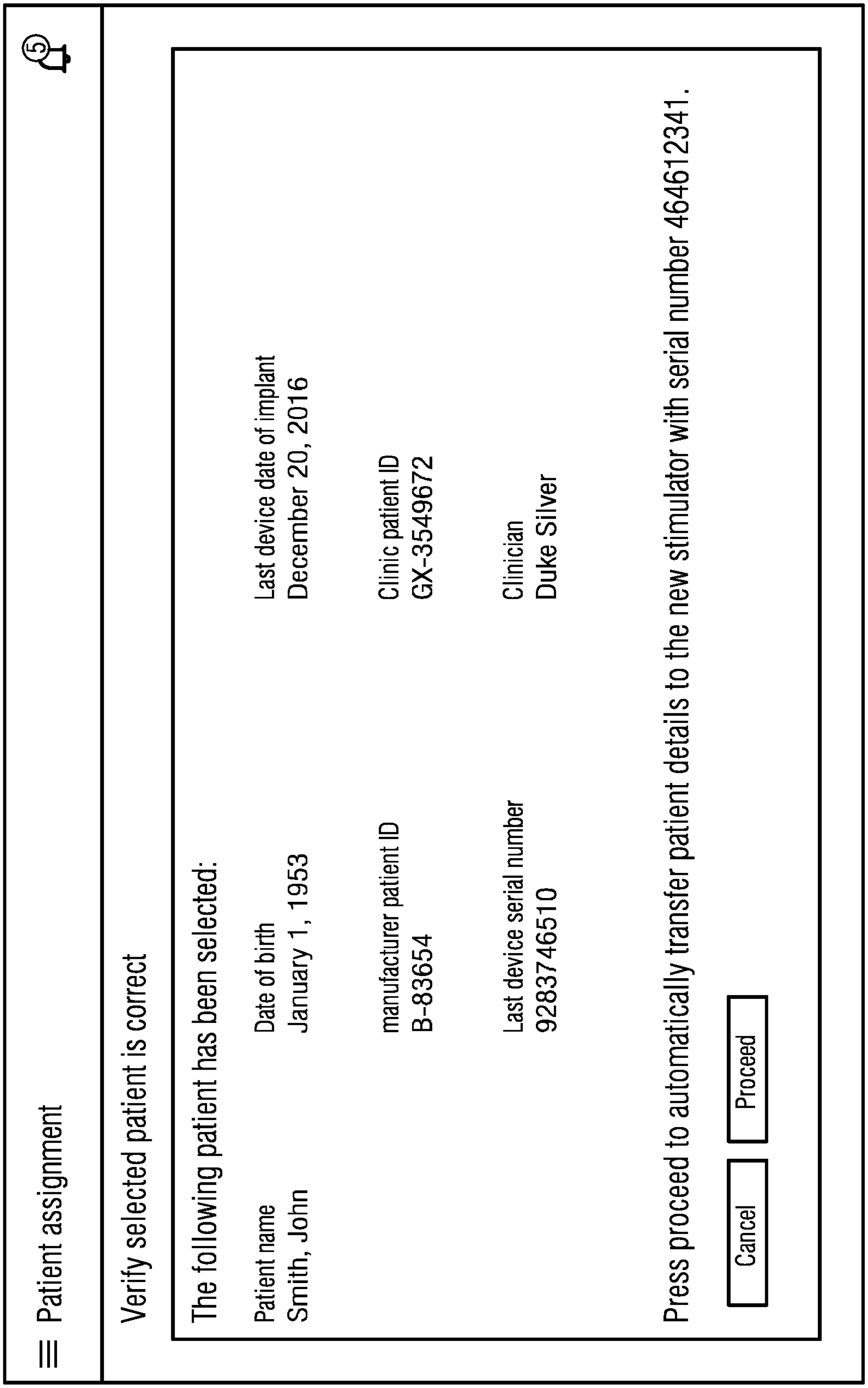
FIG. 3 Schematic representation of an exemplary embodiment of a user interface of a user device in the data system showing a patient assignment form.

FIG. 3 shows a schematic representation of an exemplary embodiment of a user interface of the user device CP in the data system 100 showing a patient assignment form. For example, after the user has registered a patient as discussed in FIGS. 2*a-b* over the user device CP, the user may manually trigger the transfer of the (entered) information to the implantable device IMP over the initial communication link. The patient assignment form may comprise a display of various patient data (e.g. patient name, date of birth, last device date of implant, etc.) which may give an overview of the (entered) information. Further, the patient assignment format may comprise a prompt to indicate to the user if he wants to proceed and write the (entered) information to the implantable device IMP by transmitting said information via the initial communication link. The user may manually activate a button (e.g. a proceed button) which may trigger the transmitting of the (entered) information to the implantable device IMP for storing the (entered) information redundantly at the two origin nodes (as outlined herein). However, the user may also cancel the transfer of the (entered) information to the implantable device (e.g. if the entered information is false and needs to be reentered).

Figure 4A:
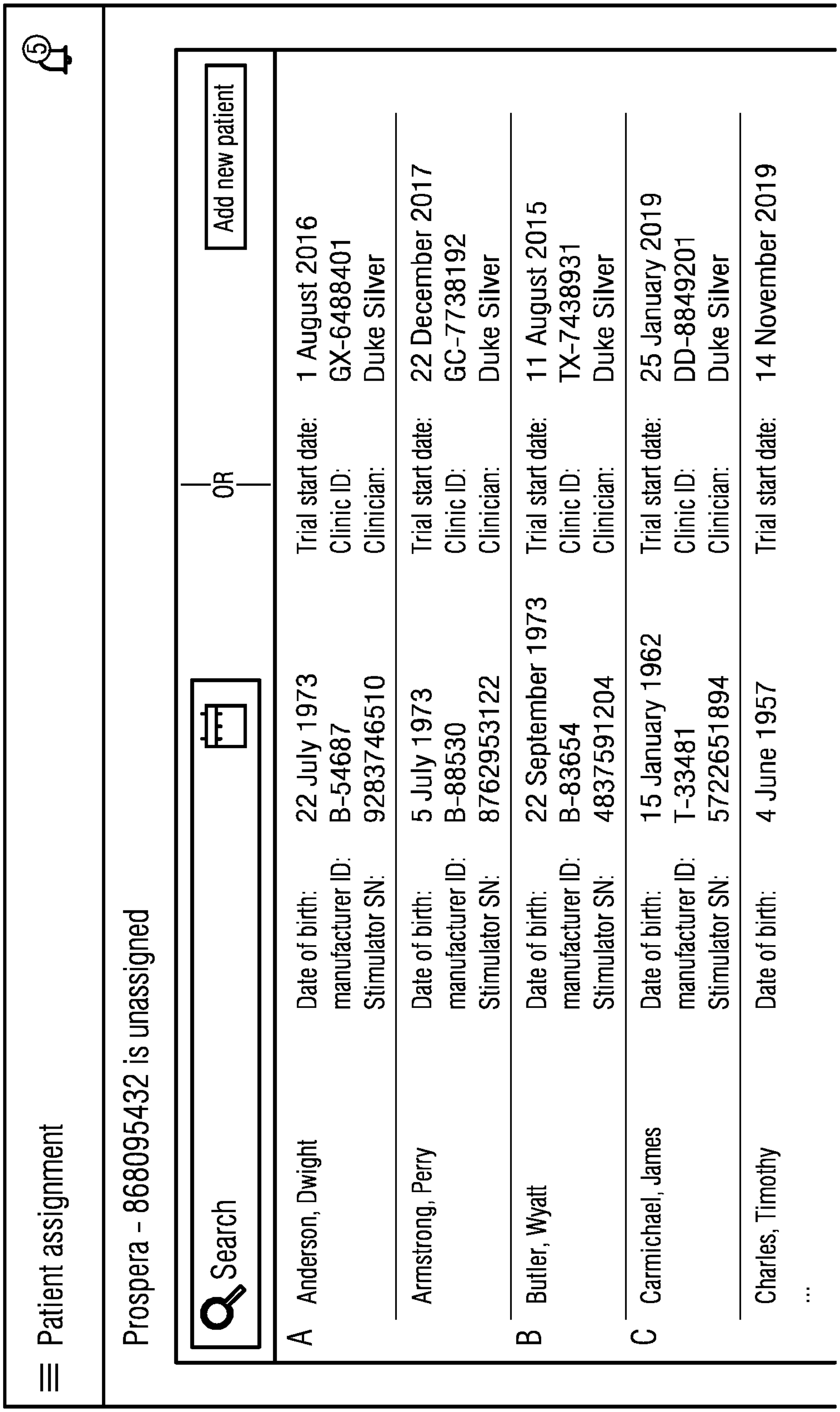
FIGS. 4*a-b* Schematic representations of an exemplary embodiment of a user interface of a user device in the data system showing a patient assignment search form.
Figure 4B:
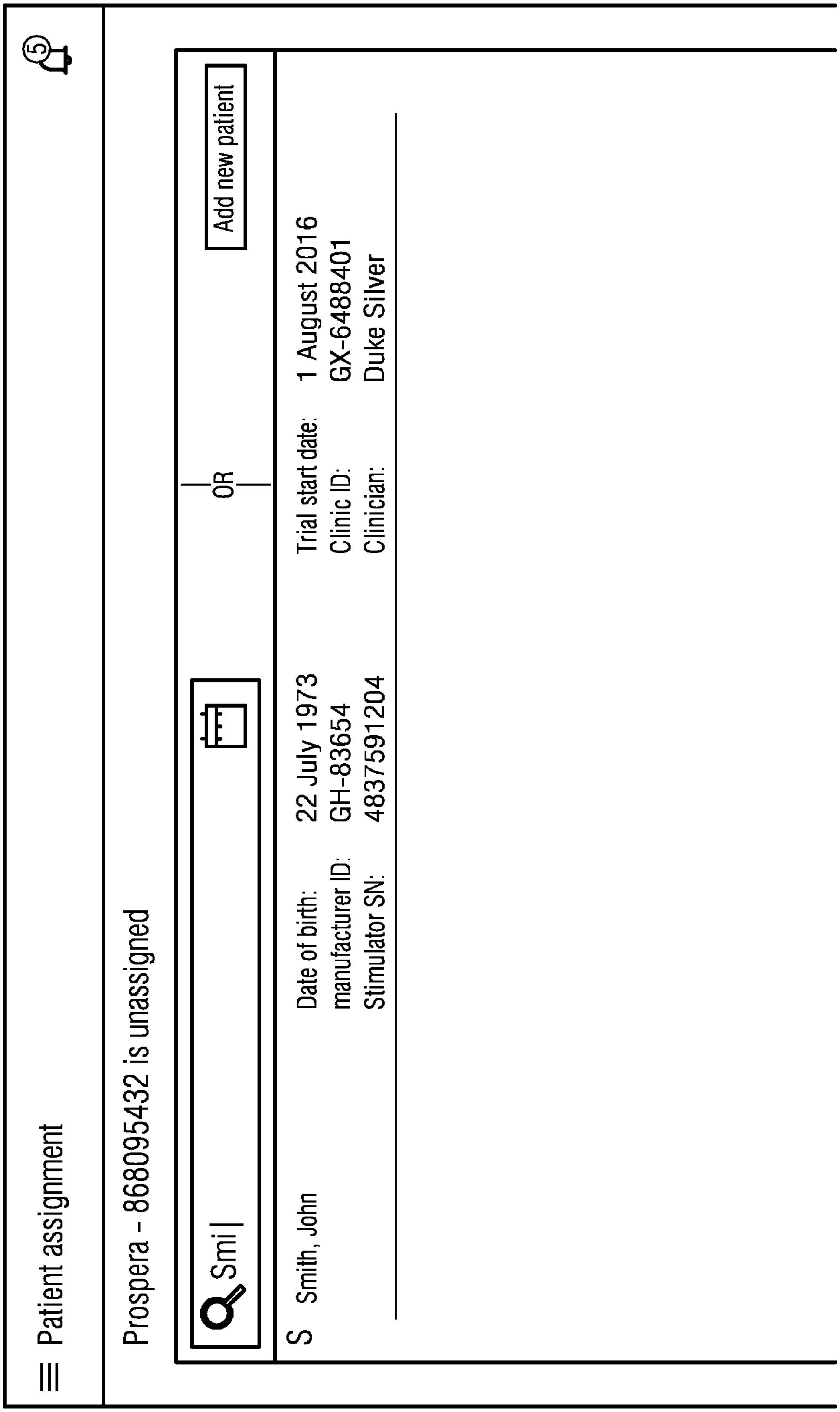

FIGS. 4*a-b* show schematic representations of an exemplary embodiment of a user interface of the user device CP in the data system 100 showing a patient assignment search form. For example, the user device CP may be configured to access a general database which may comprise a record of the information associated with the implantable device IMP for a plurality of patients. The general database may be comprised in the user device CP and/or the backend system BE. For example, the data system 100 may be configured such that it may manage the information associated with a plurality of implantable devices. For example, the data system 100 may be configured to comprise a plurality of implantable devices (e.g. a plurality of patients having the implant), a plurality of patient devices, and/or a plurality of user devices (e.g. to account for multiple clinicians, hospitals, etc.). To that regard, the backend system BE may function as the main node where the information associated with each implantable device may respectively be replicated to. It may also be conceivable that the user device may store each (entered) information which was transmitted to a specific implantable device (as outlined herein) in a general database of the user device. For example, a clinician may register ten patients a day via the user device CP which in turn may lead to ten patient records (with the respective information) in the general database of the user device CP. As seen in FIG. 4*a*, the user operating the user device may thus search for a specific patient in the general database (e.g. via name, date of birth, or any other information associated with the implantable device, etc.). The patient assignment form may initially display the patients in alphabetical order by the name of the patients. In addition, the assignment search form may display the most relevant information associated with the implantable device (e.g. patient name, manufacturer ID, implantable device serial number (e.g. stimulator serial number), clinician, etc.). As indicated in FIG. 4*b* when the user may start to enter a patient name, or a set of letters the corresponding search results (of corresponding patients) may be immediately displayed. For example, when the user may search for the last name "Smith", the according patient (or patients) may be displayed for each subset of letters inputted to the search interface (e.g. when only "Smi" is entered, the search result may immediately display every patient whose last name may start with the set of letters "Smi").

In conclusion, the invention may facilitate a variety of benefits. For example, it may enable reducing data entry points of the data system 100 to a minimum and/or it may enable an automatic data sharing between all connected data consumers (i.e. nodes of the data system). Further, it may enable implementing a data update schema that ensures that the revision of the document that is stored in the implantable device IMP (e.g. an implant and/or trial device) will always be higher or equal to the revision of the same document stored elsewhere in the data system 100. Moreover, this may be accomplished with a minimum latency and/or with state-of-the art cybersecurity. In addition, the invention may automatically accommodate for a number of clinical workflows (e.g. a registration can be initiated with or without network connection to the CP).

Further advantages may be an increased clinician satisfaction via increased ease of registration and ongoing use, patient compliance and registration process reliability; an increased patient satisfaction via increased ease of set-up and use; an increased system performance via higher registration compliance.

It will be apparent to those skilled in the art that numerous modifications and variations of the described examples and embodiments are possible in light of the above teaching. The disclosed examples and embodiments are presented for purposes of illustration only. Other alternate embodiments may include some or all the features disclosed herein. Therefore, it is the intent to cover all such modifications and alternate embodiments as may come within the true scope of this invention.

The invention claimed is:

1. A data system (100) for managing an information associated with an implantable device (IMP), the data system comprising:

the implantable device (IMP);

wherein the data system is configured as a distributed database to store the information in two or more nodes of the data system;

wherein the implantable device is configured as one of the two or more nodes, wherein the data system further comprises a user device (CP) configured for entering the information into the data system, the user device being another of the two or more nodes;

wherein the user device is configured to transmit the information to the implantable device over an initial communication link (120) substantially concurrently with the entering of the information into the user device via a replication process of the distributed database such that the information is redundantly stored and aligned on both the user device and the implantable device; and wherein the information, stored at least in part by the implantable device as one of the two or more nodes, comprises at least one information entity, the at least one information entity comprising at least one of:

patient identifiable information, follow-up information, or lead system information.

2. The data system according to claim 1, wherein the two or more nodes further comprise a backend system (BE).

3. The data system according to claim 2, wherein the user device (CP) comprises:

a user interface for receiving the information;

a storage unit for storing the information; and a transmitter for transmitting the information to the implantable device (IMP) over an initial communication link (120) between the user device (CP) and the implantable device (IMP) for storing the information in the implantable device.

4. The data system according to claim 3, wherein the data system (100) is configured such that only the user device (CP) is allowed to transmit the information to the implantable device (IMP) for storing the information in the implantable device.

5. The data system according to claim 3, wherein the user device (CP) is further configured to communicate the information to the backend system (BE) over a first communication path (110) for storing the information in the backend system (BE).

6. The data system according to claim 3, wherein the implantable device (IMP) is configured to communicate the information to the backend system (BE) over a second communication path (130, 140) for storing the information in the backend system (BE).

7. The data system according to claim 6, wherein the data system (100) is configured to instruct the implantable device (IMP) to communicate the information over the second communication path, if the first communication path is not available.

8. The data system according to claim 6, wherein the second communication path (130, 140) comprises communication from the implantable device to the backend system via a patient device (PR).

9. The data system according to claim 6, wherein the data system (100) is configured to communicate the information over the second communication path after the initial communication link between the user device (CP) and the implantable device (IMP) is terminated.

10. An implantable device (IMP), wherein the implantable device is configured as a node of a distributed database to store an information associated with the implantable device that is also stored in at least one further node of the distributed database, wherein the at least one further node is a user device (CP), and wherein the implantable device is configured to receive the information from the user device over an initial communication link substantially concurrently with the entering of the information into the user device via a replication process of the distributed database such that the information is redundantly stored and aligned on both the user device and the implantable device, and wherein the information stored by the implantable device as the node comprises at least one information entity, the at least one information entity comprising at least one of:

patient identifiable information, follow-up information, or lead system information.

11. A method for managing an information associated with an implantable device (IMP), wherein the implantable device is part of a distributed database, the method comprising:

entering the information into a user device (CP);

transmitting the information from the user device to the implantable device over an initial communication link; and storing the information in the implantable device, wherein the implantable device is configured as a node of the distributed database, wherein the transmitting and the storing occur substantially concurrently with the entering via a replication process of the distributed database to create a redundant and aligned copy of the information on the user device and the implantable device;

and wherein the information stored in the implantable device comprises at least one information entity, the at least one information entity comprising at least one of:

patient identifiable information, follow-up information, or lead system information;

the method further comprising at least one of:

communicating the information from the user device (CP) to a backend system (BE) over a first communication path; or communicating the information from the implantable device (IMP) to the backend system (BE) over a second communication path.

12. The method according to claim 11, the method further comprising at least one of the following:

communicating the information over the second communication path, if the first communication path is not available; or communicating the information over the second communication path after the initial communication link between the user device (CP) and the implantable device (IMP) is terminated.

13. The method according to claim 11, the method further comprising at least one of the following:

relating information entities which are comprised in the information to each other; or relating at least one information entity which is comprised in the information to at least one supplementary information entity which is comprised in the data system (100).

14. The method according to claim 11, the method further comprising at least one of the following:

communicating the information from the implantable device (IMP) to the backend system (BE) over the second communication path via a patient device (PR);

relating a patient device to the implantable device;

relating a patient device to the information; or relating a patient device to at least one information entity.

* * * * *